United States Patent [19]

Umezawa et al.

[11] 4,452,897
[45] Jun. 5, 1984

[54] METHOD OF PREPARING OPTICALLY ACTIVE β-(S)-AMINOGLUTARIC ACID MONOALKYL ESTERS

[75] Inventors: Hamao Umezawa, Tokyo; Masaji Ohno, Kamakura; Hirokazu Kotani; Toshinori Miyabe, both of Muko; Akira Obayashi; Osamu Tanabe, both of Uji, all of Japan

[73] Assignee: Takara Shuzo Co., Ltd., Kyoto, Japan

[21] Appl. No.: 388,475

[22] Filed: Jun. 14, 1982

[51] Int. Cl.$^3$ .................. C07B 20/00; C12R 1/20
[52] U.S. Cl. .................................. 435/280; 435/850
[58] Field of Search ............................. 435/280

[56] References Cited

PUBLICATIONS

Hirokazu Kotani et al., Agricultural and Biological Chemistry, vol. 47, No. 6, pp. 1363-1365, 1983.
Masaji Ohno et al., Journal of American Chemical Society, vol. 103, pp. 2405-2406, 1981.

*Primary Examiner*—Robert J. Warden
*Attorney, Agent, or Firm*—Wenderoth, Lind & Ponack

[57] ABSTRACT

The present invention provides a process for preparing a optically active β-(S)-aminoglutaric acid monoalkyl ester of the formula:

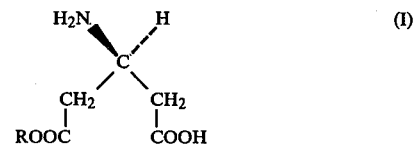

wherein R is a lower alkyl group having 1 to 4 carbon atoms, which comprises subjecting a β-N-protected aminoglutaric acid dialkyl ester of the formula:

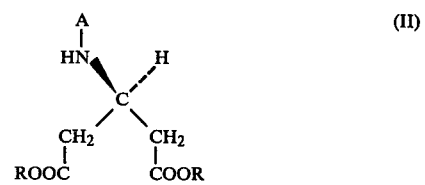

wherein each R is as defined above and A is an easily removable protecting group, to an action of an enzyme produced by a microorganism belonging to the genera Flavobacterium, Achromobacter, Xanthomonas, Alcaligenes, Serratia, Gluconobacter, Chromobacterium and Acetobacter, to selectively hydrolyze only one of the two ester groups, and then removing the protecting group.

4 Claims, No Drawings

METHOD OF PREPARING OPTICALLY ACTIVE β-(S)-AMINOGLUTARIC ACID MONOALKYL ESTERS

This invention relates to a method of preparing optically active β-(S)-aminoglutaric acid monoalkyl esters by enzymatic and chemical reactions.

More particularly, this invention relates to a method of preparing a optically active β-(S)-aminoglutaric acid monoalkyl ester of the formula:

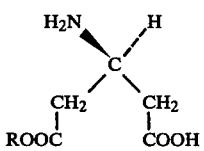

wherein R is a lower alkyl group of 1–4 carbon atoms, from a β-N-protected aminoglutaric acid dialkyl ester of the formula:

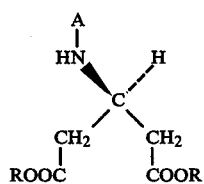

wherein R is as defined above and A is an easily removable protecting group, which comprises subjecting the dialkyl ester of the formula (II) to microbial enzymatic reaction to selectively hydrolyze only one ester linkage and then removing the protecting group.

An optically active β-(S)-aminoglutaric acid monoalkyl ester is useful as a precursor for the synthesis of (S)-4-alkoxycarbonyl-methyl-2-azetidinone which is the main moiety of carbapenam derivatives, particularly thienamycin. Although the specifically steric azetidinone can not easily be prepared by chemical processes only, the synthesis thereof can easily be accomplished when an optically active β-(S)-aminoglutaric acid monoalkyl ester is used as its precursor (Ohno et al., Japanese Patent Application No. 146344/80 which has been laid open to public on May 4, 1982 under Japanese Patent Kokai No. 71394/82).

According to said Japanese Patent Application No. 146344/80 the an optically active β-(S)-aminoglutaric acid monoalkyl ester is produced from the corresponding β-N-protected aminoglutaric acid dialkyl ester by the enzymatic and subsequent chemical procedures as shown by the following diagram:

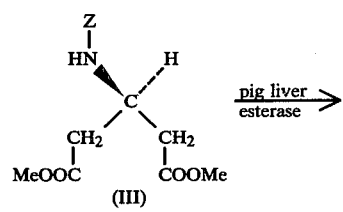

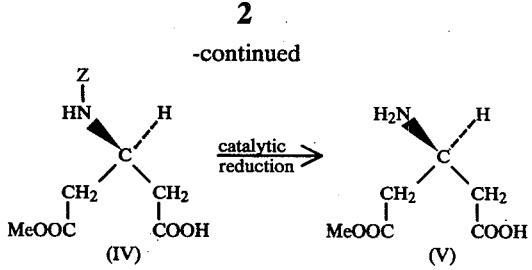

wherein Z is benzyloxycarbonyl group and Me is methyl group. Thus the optically inactive compound of the formula (III) i.e. Z-N-β-aminoglutaric acid dimethyl ester is converted into the optically active compound of the formula (IV) i.e. (S)-Z-N-β-aminoglutaric acid monomethyl ester, by the action of pig liver esterase. Then the compound of the formula (IV) is catalytically reduced with Pd-C to the compound of the formula (V) i.e. optically active β-(S)-aminoglutaric acid monomethyl ester. Therefore the reaction with pig liver esterase is most important from the view point of steric specificity. However, the source of such pig liver esterase is limited and the use thereof is industrially impractical.

In this respect we have searched for microbial esterases having same specificity as pig liver esterase. Among many kinds of microorganisms surveyed, we have found some species having high enzymatic activities with same specificity as pig liver esterase in their cells. They belong to the following genera: Flavobacterium, Achromobacter, Xanthomonas, Alcaligenes, Serratia, Gluconobacter, Chromobacterium and Acetobacter.

Thus the present invention provides a method of preparing an optically active β-(S)-aminoglutaric acid monoalkyl ester of the formula:

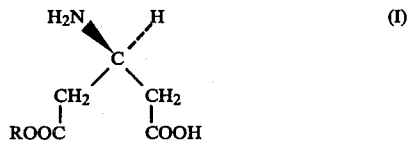

wherein R is a lower alkyl group having 1 to 4 carbon atoms, from a β-N-protected aminoglutaric acid dialkyl ester of the formula:

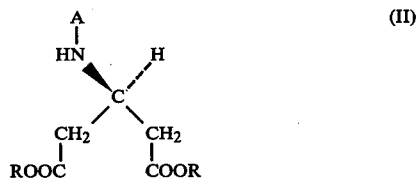

wherein each R is as defined above and A is an easily removable protecting group, which comprises subjecting the dialkyl ester of the formula (II) to an action of an enzyme produced by a microorganism belonging to the genera Flavorbacterium, Achromobacter, Xanthomonas, Alcaligenes, Serratia, Gluconobacter, Chromobacterium and Acetobacter to selectively hydrolyze only one of the two ester groups (—COOR), and then removing the protecting group A.

In the above formulae, methyl is most preferable as an alkyl group represented by R because the selective hydrolysis can be most easily effected. The protecting group (A) may be any one which can be easily removed by reduction with Pd-C, such as aralkyl or aralkyloxycarbonyl, or by moderate chemical hydrolysis such as t-butyloxycarbonyl.

Thus, R can be, e.g., methyl or ethyl, and the protecting group can be, e.g., t-butyloxycarbonyl or benzyloxycarbonyl.

As mentioned above, according to this invention, there is utilized a bacterial enzyme which is capable of selectively or specifically hydrolyzing particular one of the two ester groups —COOR in the formula (II), thereby converting the dialkyl ester (II) into the corresponding optically active monoalkyl ester.

Typical microorganisms which produce enzymes in their cells with high selective hydrolyzing activities towards the substrate to yield the half ester are, for example, Flavobacterium lutescens IFO 3084 (FERM P-6063), Archromobacter parvulus IFO 13181 (FERM P-6068), Achromobacter lyticus IFO 12725 (FERM P-6070), Alcaligenes facecalis IFO 13111 (FERM P-6069), Xanthomonas oryzae IAM 1657 (FERM P-6064), Serratia marcescens IAM 1022 (FERM P-6066), Gluconobacter dioxyacetonicus IFO 3271 (FERM P-6067), Chromobacterium chocolatum IFO 3758 (FERM P-6065) and Acetobacter aurantius IFO 3245 (FERM P-6071). These strains have been deposited at Fermentation Research Institute, Agency of Industrial Science and Technology, Japan under the above indicated FERM P numbers on July 13, 1981. Incidentally, IFO denotes the Institute for Fermentation, Osaka and IAM denotes the Institute of Applied Microbiology (Tokyo University) wherein these strains have also been deposited.

Each of the microorganisms cited above may be grown aerobically in a medium according to each nutritional requirement. Generally the medium contains an appropriate amount of carbon and nitrogen sources such as carbohydrate and protein respectively, which are easily utilized by the microorganism. Additionally the medium may also contain a trace amount of vitamins, minerals and other growth factors which are well known in the art of cultivation of microorganisms. The pH of the medium is generally in the range of 5 to 11. The cultivation temperature is 20° to 50° C. In order to promote the growth of the microorganism it is preferable to conduct the cultivation under aeration and agitation.

The enzymatic reaction i.e. the selective hydrolysis of $\beta$-N-protected aminoglutaric acid dialkyl ester of the formula (II) (sometimes referred to as "substrate" hereinafter) may be proceeded by cultivating the microorganism in a culture medium containing the substrate so that the hydrolysis is proceeded in accordance with the growth of the microorganism. Alternatively the hydrolysis may also be effected by contacting the substrate with the enzyme in a reaction mixture containing said enxyme. Thus, for example, the substrate is added to a reaction mixture containing the cells of the microorganism, culture broth, its filtrate or liquid extract of the cells obtained after the cultivation. However from the view point of recovery of the desired product after the hydrolysis reaction it is preferable to employ a concentrate obtained by the centrifugal treatment of the culture broth or cells. When the cells of the microorganism are used they may be either intact, treated with organic matters (solvents and/or detergents) or lyophilized.

In the reaction mixture any substrate concentration within the range of 0.1 to 50% (w/v) may be used. However, since the substrate is hardly soluble in water it is preferable to add a hydrophillic organic solvent (such as methanol or acetone) and/or surfactant (such as Triton X-100) in such an amount that the reaction is not inhibited, when the substrate concentration is relatively high. Even when the substrate in the reaction mixture is not completely in the dissolved state the reaction can readily proceed if the substrate is allowed to adequately contact the enzyme by a proper procedure such as aeration or agitation.

The pH of the reaction mixture is in the range of 5 to 11, preferably 7 to 8.5. When the reaction proceeds at a high substrate concentration, the pH is apt to decrease because of accumulation of the hydrolysate ($\beta$-N-protected aminoglutaric acid monoalkyl ester) in the course of progress of the hydrolysis. In such case it is preferable to adjust the pH within the optimal range with the addition of a neutralizing agent such as sodium hydroxide, potassium hydroxide, ammonia, etc.

The reaction may be conducted at a temperature of 15° to 50° C., but it is preferable to adopt optimum temperature for the enzyme of the particular microorganism used.

The reaction is continued until the desired hydrolysis is completed. After this reaction the product i.e. $\beta$-N-protected aminoglutaric acid monoalkyl ester is isolated out of the reaction mixture, prior to removing the protecting group from the product. This isolation may be carried out in any proper manner in accordance with general rule. For example, insoluble impurities such as cells are removed by filtration or centrifugation and the filtrate or supernatant is adjusted to pH 1-2 with an acid such as hydrochloric acid, sulfuric acid, citric acid or the like. Then the solution is subjected to extraction with an organic solvent such as ethyl ether, dichloromethane, ethyl acetate. The extract is dehydrated with sodium sulfate and concentrated to obtain crude crystals of the product. Further purification may be effected by column chromatography. Thus the crude crystals in chloroform are loaded on the top of a silica gel column and partitioned with a proper solvent such as a mixture of chloroform, methanol, ethyl acetate and acetic acid (90:5:5:2). The fractions containing $\beta$-N-protected aminoglutaric acid monoalkyl ester are collected and the solvent is removed therefrom in vacuo to obtain colorless crystals of pure $\beta$-N-protected aminoglutaric acid monoalkyl ester.

Then the protecting group is removed from the monoalkyl ester. This may be effected in any proper manner known for the removal of amino protecting group. Thus for example the crystals are dissolved in methanol and the solution is subjected to catalytic reduction with hydrogen in the presence of Pd-C catalyst or subjected to mild hydrolysis with trichloroacetic acid to remove the protecting group, resulting in (S)-$\beta$-aminoglutaric acid monoalkyl ester having optical rotatory of minus.

The invention will be further explained in the following Examples which, however, are given for illustration purpose only and not for limitation of the scope of the invention.

EXAMPLE 1

A culture medium containing 8% of glucose and 3.7% of brain heart infusion (Difco Co. Ltd.) was adjusted to pH 7.0 with 0.1 N sodium hydroxide. 250 ml of this medium in a Erlenmeyer flask (2 liters) was steam-sterilized at 120° C. for 15 minutes. After the sterilization 5 ml of a seed culture (which had been cultured in a test tube containing the same medium as above with the use of a microorganism indicated in Table 1) was inoculated thereon and the cultivation was conducted under agitation for 18 hours at 30° C. There were used four flasks for each microorganism so that the culture medium was one liter in total for each microorganism. The cells grown in these four flasks were harvested by centrifugation for use in the subsequent hydrolysis reaction.

The harvested cells were suspended in 48 ml of 0.15 M Tris-HCl buffer (pH 8.0) and to this suspension were added 620 mg (2 m moles) of β-benzyloxycarbonylaminoglutaric acid dimethyl ester dissolved in 2 ml of acetone. The reaction was conducted at 30° C. for 6 hours while stirring.

After the reaction the mixture was centrifuged and the supernatant was adjusted to pH 1 with hydrochloride acid. The mixture was extracted with 100 ml of dichloromethane and the extract was dehydrated over sodium sulfate and concentrated in vacuo. The concentrate was loaded on the top of a silica gel column, which had been treated with chloroform, and was eluted with a solvent mixture of chloroform, methanol, ethyl acetate and acetic acid (90:5:5:2). The fractions of the product (β-benzyloxycarbonylaminoglutaric acid monomethyl ester) were collected and the solvent was evaporated in vacuo to obtain colorless crystals.

The crystals showed the same spectra of both NMR and IR, and also showed the same Rf value (on a silica gel thin layer chromatograph developed with solvent mixture of ethyl acetate, ethanol and water in 5:1:1 ratio) as the product obtained by Ohno et al in Japanese Patent Application No. 146344/80 and were identified to be β-(S)-benzyloxycarbonylaminoglutaric acid monomethyl ester. Further, the specific optical rotation, i.e. $[\alpha]_D^{20}$ (C=7, CHCl$_3$), of each of the products produced by the enzymatic reaction with grown cells of each of the various microorganisms was in the range of from +0.53 to +0.66 as shown in Table 1. From these results each of the products was confirmed to be β-(S)-N-benzyloxycarbonylaminoglutaric acid monomethyl ester described by Ohno et al (Japanese Patent Application No. 146344/80).

250 mg (0.85 m moles) of each of the isolated products were dissolved in 20 ml of methanol and the solution was added with 40 mg of Pd-C (10%) and agitated for 30 minutes while introducing hydrogen gas. The reaction mixture was filtered and the filtrate was concentrated to obtain colorless crystals with the respective yields shown in Table 1. Each product was identified to be β-(S)-aminoglutaric acid monomethyl ester as it showed same spectra both of NMR and IR as those described by Ohno et al (Japanese Patent Application No. 146344/80), and the specific optical rotation, i.e. $[\alpha]_D^{25}$ (C=3, H$_2$O) was in the range of from −5.32 to −5.48 as shown in Table 1.

TABLE 1

| Microorganism | β-(S)-benzyloxycarbonylaminoglutaric acid monomethyl ester* | | β-(S)-aminoglutaric acid monomethyl ester** | |
|---|---|---|---|---|
|  | Yield (mg) | $[\alpha]_D^{20}$ | Yield (mg) | $[\alpha]_D^{25}$ |
| Flavobacterium lutescens IFO 3084 | 543 | +0.62 | 92 | −5.34 |
| Achromobacter parvulus IFO 13181 | 540 | +0.66 | 116 | −5.39 |
| Achromobacter lyticus IFO 12725 | 470 | +0.53 | 87 | −5.48 |
| Alcaligenes faecalis IFO 13111 | 225 | +0.56 | 95 | −5.34 |
| Xanthomonas oryzae IAM 1657 | 246 | +0.62 | 110 | −5.40 |
| Gluconobacter dioxyacetonicus IFO 3271 | 325 | +0.60 | 103 | −5.32 |
| Chromobacterium chocolatum IFO 3758 | 151 | +0.56 | 96 | −5.45 |
| Serratia marscens IAM 1022 | 62 | +0.60 | 88 | −5.39 |
| Acetobacter Aurantius IFO 3245 | 92 | +0.60 | 92 | −5.40 |

Remarks:
*Yield from 620 mg (2 m moles) of β-N—benzyloxycarbonylaminoglutaric acid dimethyl ester by enzymatic reaction
**Yield from 250 mg (0.85 m moles) of β-(S)—N—benzyloxycarbonylaminoglutaric acid monomethyl ester by catalytic reduction

EXAMPLE 2

Each of Flavobacterium lutescens IFO 3084 and Achromobacter parvulus IFO 13181 was cultured and the grown cells were collected in the same manner as in Example 1. By the use of the grown cells the enzymatic relation was conducted in the same manner as in Example 1 except that 550 mg (2 m moles) of β-N-butyloxycarbonylaminoglutaric acid dimethyl ester were used as the substrate in the reaction mixture.

After the enzymatic reaction the supernatant obtained by the centrifugation of the reaction mixture was adjusted to pH 2 with citric acid and was extracted with ethyl ether. Ether was evaporated in vacuo from the extract and the concentrate was treated in the same manner as in Example 1 to obtain colorless crystals.

The protecting group was removed through hydrolysis with trifluoroacetic acid, and the resulting hydrolysate was concentrated in vacuo to obtain colorless crystals with the respective yields shown in Table 2.

In NMR and IR spectra these two products were coincident to the product described by Ohno et al in Japanese Patent Application No. 146344/80, and their specific optical rotations, i.e. $[\alpha]_D^{25}$ (C=3, H$_2$O) were −5.42 and −5.35 respectively as shown in Table 2. From these results these products were identified to be β-(S)-aminoglutaric acid monomethyl ester.

TABLE 2

| Microorganism | β-(S)—aminoglutaric acid monomethyl ester | |
|---|---|---|
|  | Yield (mg)* | $[\alpha]_D^{25}$ (C = 3, H$_2$O) |
| Flavobacterium lutescens IFO 3084 | 205 | −5.42 |
| Achromobacter | 129 | −5.35 |

TABLE 2-continued

| | β-(S)—aminoglutaric acid monomethyl ester | |
|---|---|---|
| Microorganism | Yield (mg)* | $[\alpha]_D^{25}$ (C = 3, H$_2$O) |
| parvulus IFO 13181 | | |

Remark:
*Yield from 550 mg (2 m moles) of β-N—t-butyloxy-carbonylaminoglutaric acid dimethyl ester

EXAMPLE 3

Flavobacterium lutescens IFO 3084 was cultured in 1 liter medium and the grown cells were collected in the same manner as in Example 1. The collected cells were lyophilized and used as enzyme source in a reaction mixture (50 ml) containing 1240 mg (4 m moles) of β-N-benzyloxycarbonylaminoglutaric acid dimethyl ester as substrate and other ingredients as in Example 1. The enzyme reaction was conducted at 30° C. for 12 hours with shaking.

After the enzyme reaction the product was isolated in the same manner as in Example 1 to obtain 752 mg of colorless crystals, $[\alpha]_D^{20}$ (C=7, CHCl$_3$)= +0.58.

Then 250 mg of the above crystals were subjected to catalytic reduction and treated in the same manner as in Example 1 to obtain 85 mg of colorless crystals. The specific optical rotation thereof, i.e. $[\alpha]_D^{25}$ (C=3, H$_2$O) was −5.40.

What is claimed is:

1. A process for preparing an optically active β-(S)-aminoglutaric acid monoalkyl ester of the formula:

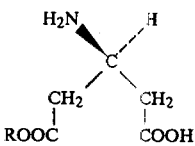

wherein R is a lower alkyl group having 1 to 4 carbon atoms, which comprises subjecting a β-N-protected aminoglutaric acid dialkyl ester of the formula:

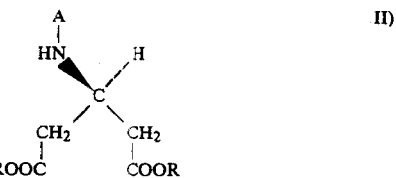

wherein each R is as defined above and A is an easily removable protecting group, to hydrolysis by an enzyme produced by Flavobacterium lutescens IFO 3084 (FERM P-6063) or Gluconobacter dioxyacetonicus IFO 3271 (FERM P-6067) to selectively hydrolyze only one of the two ester groups, removing the protecting group, and then recovering said monoalkyl ester.

2. A process according to claim 1 wherein the microbial enzyme reaction is conducted by the use of culture broth, intact cells or treated cells of said microorganism as the source of the enzyme.

3. A process according to claim 1 wherein the protecting group in the formula (II) is benzyloxycarbonyl and the alkyl group is either methyl or ethyl.

4. A process according to claim 1 wherein the protecting group in the formula (II) is t-butyloxycarbonyl and the alkyl group is either methyl or ethyl.

* * * * *